United States Patent
Ma

(10) Patent No.: US 9,615,891 B2
(45) Date of Patent: Apr. 11, 2017

(54) STERILITY COVER FOR MEDICAL DEVICE SURFACE

(71) Applicant: Richard Ma, Carlisle, MA (US)

(72) Inventor: Richard Ma, Carlisle, MA (US)

(*) Notice: Subject to any disclaimer, the term of this patent is extended or adjusted under 35 U.S.C. 154(b) by 0 days.

(21) Appl. No.: 14/703,357

(22) Filed: May 4, 2015

(65) Prior Publication Data
US 2015/0320499 A1 Nov. 12, 2015

Related U.S. Application Data

(60) Provisional application No. 61/991,666, filed on May 12, 2014.

(51) Int. Cl.
| B65D 33/00 | (2006.01) |
| A61B 46/10 | (2016.01) |
| A61B 19/02 | (2006.01) |
| A61B 7/02 | (2006.01) |
| A61B 50/20 | (2016.01) |

(52) U.S. Cl.
CPC ........... *A61B 46/10* (2016.02); *A61B 7/02* (2013.01); *A61B 19/026* (2013.01); *A61B 50/20* (2016.02); *B65D 33/001* (2013.01); *A61B 2019/0201* (2013.01); *A61B 2019/0267* (2013.01); *A61B 2562/247* (2013.01)

(58) Field of Classification Search
CPC ......... A45C 13/002; A61B 7/02; A61B 19/02; A61B 19/026; A61B 2019/0201; A61B 2019/0267; A61B 2562/247; B65D 25/34; B65D 29/00; B65D 33/00; B65D 33/001; B31B 19/90

USPC ................ 206/305, 320, 363, 438; 150/154; 181/131, 137, 141; 600/586; 383/84–87

See application file for complete search history.

(56) References Cited

U.S. PATENT DOCUMENTS

| 3,318,444 A | 5/1967 | Weicher et al. |
| 3,771,645 A | 11/1973 | Wendel |
| 4,006,823 A | 2/1977 | Soto |
| 4,793,486 A * | 12/1988 | Konopka ............ A61M 5/1417 206/305 |
| 4,871,046 A | 10/1989 | Turner |
| 5,119,968 A | 6/1992 | Palmer |

(Continued)

OTHER PUBLICATIONS

U.S. Office Action dated Apr. 25, 2012, issued in U.S. Appl. No. 13/176,037.

*Primary Examiner* — Bryon Gehman
(74) *Attorney, Agent, or Firm* — Polsinelli PC

(57) ABSTRACT

A disposable bag for maintaining sterility of a medical instrument having a detection mechanism and cable extending from the detection mechanism,
wherein the bag comprises:
a pair of flexible sheets comprised of a polymeric material,
the pair of sheets being arranged in parallel to each other and sealed along opposing lateral sides that extend longitudinally from a top end to a bottom end,
the cable having a selected length such that upon insertion of the detection mechanism through the enclosed interior chamber of the bag, the cable extends longitudinally through the open bottom end,
the bag being adapted to be attached to at least a portion of the cable that extends from the detection mechanism downstream toward the open bottom end.

8 Claims, 7 Drawing Sheets

(56) References Cited

U.S. PATENT DOCUMENTS

| | | | |
|---|---|---|---|
| 5,172,683 A * | 12/1992 | West | A61B 7/02 181/131 |
| 5,486,659 A | 1/1996 | Rosenbush | |
| 5,619,992 A * | 4/1997 | Guthrie | A61B 5/14552 356/41 |
| 5,747,751 A * | 5/1998 | Weckerle | A61B 7/02 181/131 |
| 6,467,568 B1 | 10/2002 | Kemper | |
| 7,117,971 B1 | 10/2006 | Cornacchia | |
| 7,614,477 B2 | 11/2009 | Statner et al. | |
| 7,806,267 B2 | 10/2010 | Pack-Walden et al. | |
| 2012/0010517 A1 | 1/2012 | Ma | |

* cited by examiner

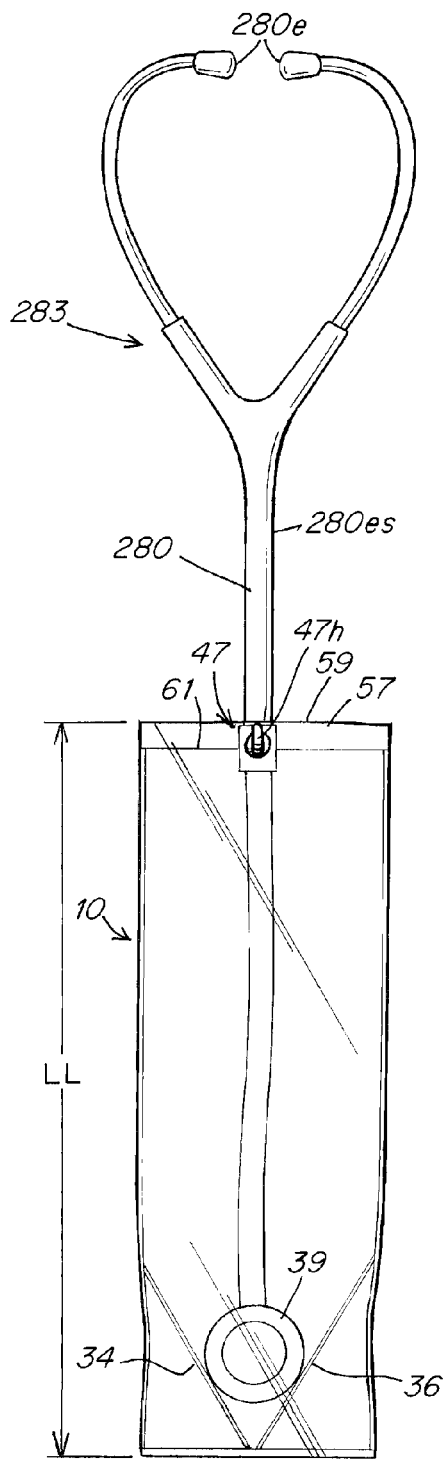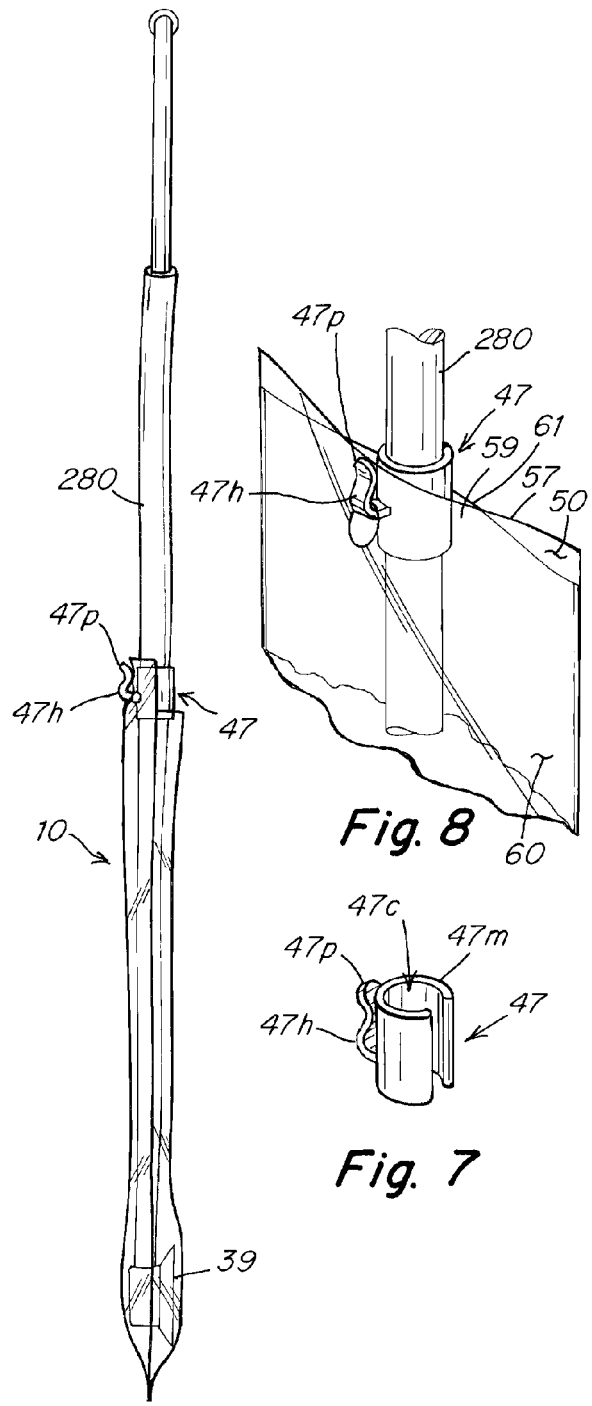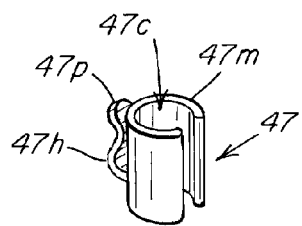
Fig. 5
Fig. 6
Fig. 8
Fig. 7

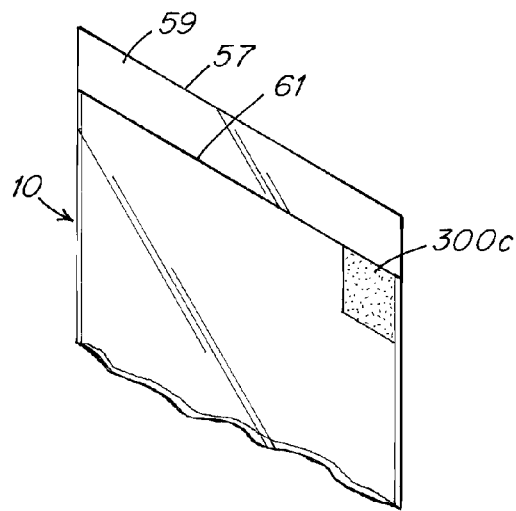
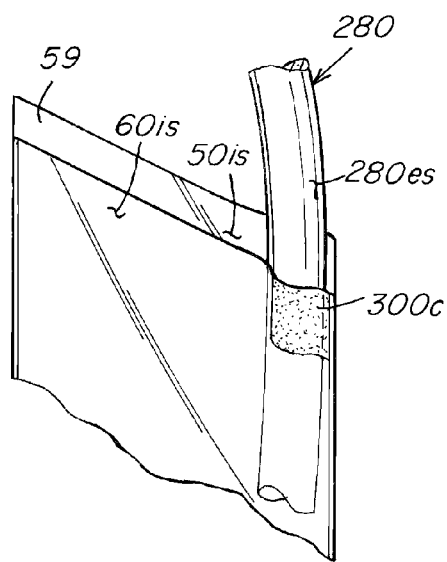
Fig. 13  Fig. 14
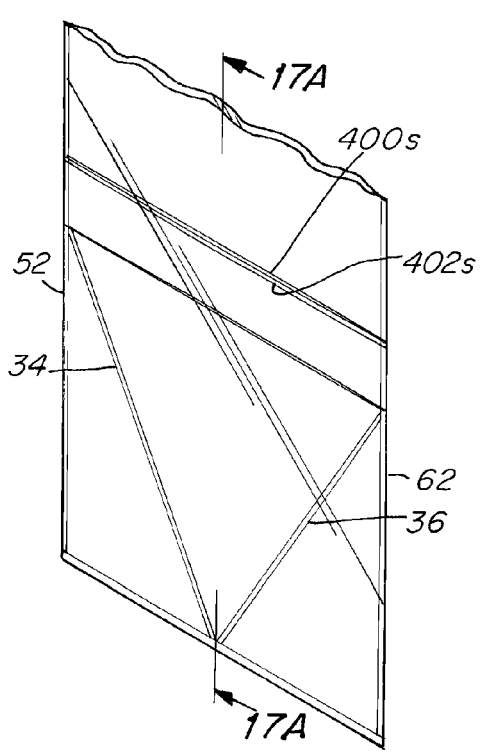
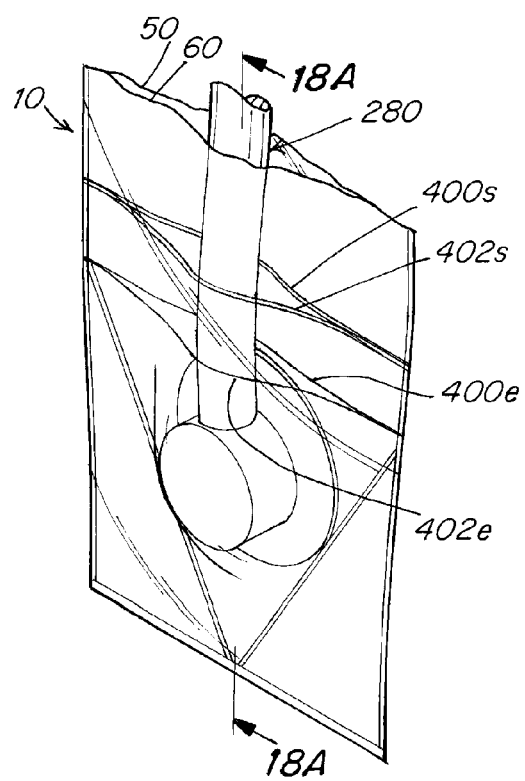
Fig. 15  Fig. 16

STERILITY COVER FOR MEDICAL DEVICE SURFACE

RELATED APPLICATIONS

This application claims the benefit of priority to U.S. Provisional Patent Application Ser. No. 61/991,666 entitled Serially Deliverable Cover For Medical Device Surface, filed May 12, 2014, the disclosure of which is incorporated herein by reference in its entirety.

BACKGROUND

Medical devices, instruments, implements and the like are commonly used by doctors, nurses and health care providers generally on multiple patients. Devices such as stethoscopes, blood pressure measurement devices, electrodes and the like are used to make contact with some portion of the surface of multiple patients one after the other without thought for sterilization in advance of use or, if sterilization is immediately available for use, is ignored by the health care provider due to the seemingly low risk of contamination of the device being used.

SUMMARY OF INVENTION

Health care providers and physicians often see how hospitalization can be harmful to a subject's health. The number of hospital acquired infections are quite alarming. Health care providers are typically very careful to hand wash their hands between attending to successive patients. Health care providers often isolate patients with very resistant infections and sanitize the room when the infected patient is discharged. Notwithstanding such precautions, a major culprit in spreading infection between successive patients is the stethoscope. Health care providers put it around their necks in close proximity to their own exhaled breath.

Stethoscopes physically touch every patient that a health care provider normally sees and rarely is a stethoscope cleaned with alcohol. In a typical day in a hospital every patient is seen by at least 3-4 nurses (due to shift changes), 1-3 physicians (depending on whether a specialist are involved or not), 2-3 nurse's aids (taking vital signs), and possibly a few respiratory therapists. This number is much higher in teaching hospitals because of exposure to medical students and student nurses. The stethoscope touches one patient up to 10 times a day. This means just by random chance a single patient can actually have contact with a total stranger in another floor of the hospital more than once without ever knowing it. Covers for stethoscopes have been devised but have not been practicable in the mechanisms, if any, for accessibility or ease of use.

Although bags or covers have been used for covering stethoscopes such as disclosed in U.S. patent publication no. 20120010517, such prior bags or devices cannot dispose the examination detection head in any given position within the bag and cannot ensure that the detection mechanism or the cable extending from the detection mechanism will remain in the bag in a stable location or otherwise once inserted.

In accordance with the invention there is provided a disposable bag 10 for maintaining sterility of a medical instrument 283, the instrument 283 comprising an elongated cable 280 having a cable length LL and a detection mechanism 39 for engagement with an examination surface of a subject to be examined for a signal generated by the subject through the examination surface, the elongated cable 280 being interconnected to the detection mechanism 39 at a proximal end of the cable for transmitting a signal generated by the detection mechanism 39 to a distal end 280e of the cable, wherein the bag 10 comprises:

a pair of flexible sheets 50, 60 comprised of a polymeric material, the sheets having a thickness through which the detection mechanism 39 can sense the signal generated by the subject when the detection mechanism is held in engagement against the examination surface with one of the sheets 50, 60 disposed between the detection mechanism and the examination surface, the pair of sheets being arranged in parallel to each other and sealed along opposing lateral sides 52, 62 that extend longitudinally LO from a top end 40 to a bottom end 57, 61, the top end 40 being sealed and the bottom end 57, 61 being open such that the sheets form an enclosed interior chamber 55 with an open longitudinal bottom end for insertion of the detection mechanism into and longitudinally LO through the enclosed interior chamber 55 a selected insertion distance from the open bottom end 57, 61 toward the sealed top end 40, one 50 of the pair of sheets being longer longitudinally than the other 60 of the pair sheets forming a flap 59 that extends from the one longer sheet to a longer bottom edge 57 that extends longitudinally beyond a shorter bottom edge 61 of the other of the pair of sheets, the bag 10 having a selected longitudinal length LL relative to the cable length such that upon insertion of the detection mechanism 39 through the enclosed interior chamber 55 along the selected insertion distance, the cable extends longitudinally LO from the detection mechanism 39 through the enclosed interior chamber 55 and further through the open bottom end to at least the longer bottom edge 57 of the one longer sheet 50, the flap 59 being adapted to be attached 47h, 47p, 300, 304 to at least a portion 280es of the cable that extends from the detection mechanism to at least the longer bottom edge 61 such that the detection mechanism is held within the enclosed interior chamber 55 by said attachment 47h, 47p, 300, 304.

The flap 59 can have a layer of adhesive material 300, 304 disposed on an interior surface of the flap in a selected two dimensional pattern and the cable has an outside surface 280es that is adhesively attachable to the adhesive material, the layer of adhesive material being disposed on the interior surface 59is of the flap in an arrangement such that at least a portion of the outside surface 280es of the cable that extends to at least the longer bottom edge 61 of the one longer sheet of the bag is manually compressible against at least a portion of the adhesive layer and adhesively attachable thereto.

The flap typically has a lateral width W, the adhesive material being disposed on the interior surface 59IS of the flap 59 in an arrangement such that the adhesive material extends laterally LAT along substantially the entire lateral width W of the flap.

A thin sheet or strip of non-adhesive material 302 that is complementary to the selected two dimensional pattern of the adhesive material is typically deposited over and adhered to the layer of adhesive material 300, 304, the thin sheet or strip being adapted to be readily peeled off 302e of the adhesive material by hand.

The cable can have a hook 47h connected 47m, 47c to the cable 280, the hook 47h including a puncture member 47p that is adapted to readily puncture through the flap 59 on application of manual force directing the puncture member 47p against the interior surface 59is of the flap, the hook 47h being connected 47*m*, 47*c* to the cable at a position downstream from the detection mechanism.

The pair of sheets can be sealed together between the opposing lateral sides 52, 62 and the top and bottom ends along one or more seam lines 34, 36, 34*a*, 34*b*, 36*b*, 36*c* that are arranged in a pattern that engage and hold the detection mechanism to define the selected insertion distance of the detection mechanism when the detection mechanism is inserted through the open bottom end longitudinally through the enclosed interior chamber 55 toward the top end 40 as far as the detection mechanism can be moved longitudinally.

The seam lines are typically arranged in a pattern that engage and hold the detection mechanism to define a maximum distance of longitudinal insertion against travel toward the top end when the detection mechanism is inserted through the enclosed interior and moved toward the top end within the interior as far toward the top end as the detection mechanism can be moved.

The one or more seam lines are preferably disposed between the sides of the bag in an arrangement that slidably engages the detection mechanism when the detection mechanism is inserted through the enclosed interior and moved toward the top end.

The detection mechanism typically has a longest dimension of certain distance, the seam lines being disposed between the sides of the bag a maximum distance apart from each other or from the sides of the bag, that is less than the distance of the longest dimension of the detection mechanism such that the detection mechanism engages against and is held by the seam lines on longitudinal insertion.

The seam lines preferably comprise a pair of separate lines formed as mirror images 34, 36 of each other around a longitudinal center C of the enclosure, the seam lines being arranged such that the detection mechanism is routed between the seam lines on longitudinal movement of the detection mechanism from the bottom end toward the top end.

The seam lines typically form a generally triangular or conical space between the seam lines within the interior of the enclosure.

The triangular or conical space is preferably truncated at its top end.

The sealed top end is typically attached along a line of perforations 30, 32 to a manifold 15, the perforations enabling manual tearing away of the bag from the manifold.

In another aspect of the invention there is provided a In another aspect of the invention there is provided a method of examining a patient with a medical instrument having a cable and detection mechanism as described immediately above wherein the detection mechanism detects a selected signal generated by patient, the method comprising inserting the detection mechanism in a bag as described immediately above, attaching the cord to the layer of adhesive material and examining the patient with the detection mechanism inserted in the bag.

In another aspect of the invention there is provided a disposable bag for maintaining sterility of a medical instrument, the instrument comprising an elongated cable having a cable length and a detection mechanism for engagement with an examination surface of a subject to be examined for a signal generated by the subject through the examination surface, the elongated cable being interconnected to the detection mechanism at a proximal end of the cable for transmitting a signal generated by the detection mechanism to a distal end of the cable, wherein the bag comprises:

a pair of flexible sheets comprised of a polymeric material, the sheets having a thickness through which the detection mechanism can sense the signal generated by the subject when the detection mechanism is held in engagement against the examination surface with one of the sheets disposed between the detection mechanism and the examination surface, the pair of sheets being arranged in parallel to each other and sealed along opposing lateral sides that extend longitudinally from a top end to a bottom end, the top end being sealed and the bottom end being open such that the sheets form an enclosed interior chamber with an open longitudinal bottom end for insertion of the detection mechanism into and longitudinally through the enclosed interior chamber a selected insertion distance from the open bottom end toward the sealed top end, the pair of sheets each having an interior surface facing each other, one or the other of the interior surfaces having a layer of adhesive material disposed thereon in a selected two dimensional pattern at a longitudinal position between the top and bottom ends such that the adhesive material on an interior surface of one sheet opposes and can make contact with the interior surface of an opposing sheet, the bag having a selected longitudinal length relative to the cable length such that upon insertion of the detection mechanism through the enclosed interior chamber along the selected insertion distance, the cable extends longitudinally from the detection mechanism through the enclosed interior chamber and further through the open bottom end to at least the longer bottom edge of the one longer sheet, the cable having an outside surface that is adhesively attachable to the adhesive material, the layer of adhesive material being disposed on the interior surface of the flap at a selected longitudinal position less than the selected insertion distance in an arrangement such that at least a portion of the outside surface of the cable that extends from the detection mechanism longitudinally to at least the selected longitudinal position of the adhesive material is manually compressible against and adhesively attachable to the adhesive material.

The adhesive material of such a bag can be disposed on both of the interior surfaces of the opposing sheets of the bag in the selected two dimensional pattern.

The pair of sheets of such a bag are typically sealed together between the opposing lateral sides and the top and bottom ends along one or more seam lines that are arranged in a pattern that engage and hold the detection mechanism to define the selected insertion distance of the detection mechanism when the detection mechanism is inserted through the open bottom end longitudinally through the enclosed interior chamber toward the top end as far as the detection mechanism can be moved longitudinally.

Such a bag typically has a lateral width, the adhesive material being disposed on or the or the other or both of the interior surfaces of the opposing sheets in an arrangement such that the adhesive material extends laterally along substantially the entire lateral width.

A thin sheet or strip of non-adhesive material that is complementary to the selected two dimensional pattern is preferably deposited over and adhered to the layer of adhesive material, the thin sheet or strip being adapted to be readily peeled off of the adhesive material by hand.

The seam lines of such a bag are preferably arranged in a pattern that engage and hold the detection mechanism to define a maximum distance of longitudinal insertion against travel toward the top end when the detection mechanism is inserted through the enclosed interior and moved toward the top end within the interior as far toward the top end as the detection mechanism can be moved.

The one or more seam lines of such a bag are preferably disposed between the sides of the bag in an arrangement that slidably engages the detection mechanism when the detection mechanism is inserted through the enclosed interior and moved toward the top end.

The detection mechanism of such a bag preferably has a longest dimension of certain distance, the seam lines being disposed between the sides of the bag a maximum distance apart from each other or from the sides of the bag, that is less than the distance of the longest dimension of the detection mechanism such that the detection mechanism engages against and is held by the seam lines on longitudinal insertion.

The seam lines of such a bag preferably comprise a pair of separate lines formed as mirror images of each other around a longitudinal center of the enclosure, the seam lines being arranged such that the detection mechanism is routed between the seam lines on longitudinal movement of the detection mechanism from the bottom end toward the top end.

The seam lines typically form a generally triangular or conical space between the seam lines within the interior of the enclosure.

The triangular or conical space is preferably truncated at its top end.

The the sealed top end of such a bag can be attached along a line of perforations to a manifold, the perforations enabling manual tearing away of the bag from the manifold.

In another aspect of the invention there is provided a method of examining a patient with a medical instrument having a cable and detection mechanism as described immediately above wherein the detection mechanism detects a selected signal generated by patient, the method comprising inserting the detection mechanism in a bag as described immediately above, attaching the cord to the layer of adhesive material and examining the patient with the detection mechanism inserted in the bag.

In another aspect of the invention there is provided a disposable bag for maintaining sterility of a medical instrument, the instrument comprising an elongated cable having a cable length and a detection mechanism for engagement with an examination surface of a subject to be examined for a signal generated by the subject through the examination surface, the elongated cable being interconnected to the detection mechanism at a proximal end of the cable for transmitting a signal generated by the detection mechanism to a distal end of the cable, wherein the bag comprises:

a pair of flexible sheets comprised of a polymeric material, the sheets having a thickness through which the detection mechanism can sense the signal generated by the subject when the detection mechanism is held in engagement against the examination surface with one of the sheets disposed between the detection mechanism and the examination surface, the pair of sheets being arranged in parallel to each other and sealed along opposing lateral sides that extend longitudinally from a top end to a bottom end, the top end being sealed and the bottom end being open such that the sheets form an enclosed interior chamber with an open longitudinal bottom end for insertion of the detection mechanism into and longitudinally through the enclosed interior chamber a selected insertion distance from the open bottom end toward the sealed top end, one of the pair of sheets being longer longitudinally than the other of the pair sheets forming a flap that extends from the one longer sheet to a longer bottom edge that extends longitudinally beyond a shorter bottom edge of the other of the pair of sheets, the bag having a selected longitudinal length relative to the cable length such that upon insertion of the detection mechanism through the enclosed interior chamber along the selected insertion distance, the cable extends longitudinally from the detection mechanism through the enclosed interior chamber and further through the open bottom end to at least the longer bottom edge of the one longer sheet, wherein the flap has a layer of adhesive material disposed on an interior surface of the flap in a selected two dimensional pattern and the cable has an outside surface that is adhesively attachable to the adhesive material, the layer of adhesive material being disposed on the interior surface of the flap in an arrangement such that at least a portion of the outside surface of the cable that extends to at least the longer bottom edge of the one longer sheet of the bag is manually compressible against at least a portion of the adhesive layer and adhesively attachable thereto.

The flap of such a bag typically has a lateral width, the adhesive material being disposed on the interior surface of the flap in an arrangement such that the adhesive material extends laterally along substantially the entire lateral width of the flap.

A thin sheet or strip of non-adhesive material that is complementary to the selected two dimensional pattern is preferably deposited over and adhered to the layer of adhesive material, the thin sheet or strip being adapted to be readily peeled off of the adhesive material by hand.

The pair of sheets of such a bag are typically sealed together between the opposing lateral sides and the top and bottom ends along one or more seam lines that are arranged in a pattern that engage and hold the detection mechanism to define the selected insertion distance of the detection mechanism when the detection mechanism is inserted through the open bottom end longitudinally through the enclosed interior chamber toward the top end as far as the detection mechanism can be moved longitudinally.

The seam lines of such a bag are preferably arranged in a pattern that engage and hold the detection mechanism to define a maximum distance of longitudinal insertion against travel toward the top end when the detection mechanism is inserted through the enclosed interior and moved toward the top end within the interior as far toward the top end as the detection mechanism can be moved.

The one or more seam lines of such a bag are preferably disposed between the sides of the bag in an arrangement that slidably engages the detection mechanism when the detection mechanism is inserted through the enclosed interior and moved toward the top end.

The detection mechanism preferably has a longest dimension of certain distance, the seam lines being disposed between the sides of the bag a maximum distance apart from each other or from the sides of the bag, that is less than the distance of the longest dimension of the detection mechanism such that the detection mechanism engages against and is held by the seam lines on longitudinal insertion.

The seam lines of such a bag preferably comprise a pair of separate lines formed as mirror images of each other around a longitudinal center of the enclosure, the seam lines being arranged such that the detection mechanism is routed between the seam lines on longitudinal movement of the detection mechanism from the bottom end toward the top end.

The seam lines preferably form a generally triangular or conical space between the seam lines within the interior of the enclosure.

The triangular or conical space is preferably truncated at its top end.

The sealed top end is typically attached along a line of perforations to a manifold, the perforations enabling manual tearing away of the bag from the manifold.

In another aspect of the invention there is provided a method of examining a patient with a medical instrument having a cable and detection mechanism as described immediately above wherein the detection mechanism detects a selected signal generated by patient, the method comprising inserting the detection mechanism in a bag as described immediately above, attaching the cord to the layer of adhesive material and examining the patient with the detection mechanism inserted in the bag.

The present invention also provides a collection of enclosed bags sequentially arranged in a stack, one-next-to-each-other commonly attached to a support that can be readily hung on a rail or other stationary support in an examination room. Each individual bag preferably comprises two opposing sheets attached along two opposing continuous edges of polymer material and attached at one closed end to successive manifold portions of plastic material which in turn are attached to the support.

The present invention provides an apparatus and method for preventing contact between the ambient environment and/or the surface of a living subject (e.g. human being or an animal) and the operative surface of a medical instrument or component thereof that is supposed to be placed in contact with or in close proximity to the surface of the subject. The apparatus of the invention comprises a cover into which the operative surface of the medical instrument such as a stethoscope can be inserted so as to prevent microorganisms, chemicals or other matter that might reside on the surface of the instrument from making contact with the subject.

In accordance with the invention there is provided an enclosure for a medical instrument having a detection mechanism for engagement with an examination surface of a subject to be examined for a signal generated by the subject, the enclosure comprising:

a pair of flexible sheets having a thickness that renders the sheets transmissive to the signal generated by the subject, the pair of sheets being arranged in parallel to each other and sealed along opposing lateral sides extending longitudinally from a top end to a bottom end, the top end being sealed and the bottom end being open such that the sheets form an enclosed bag having an enclosed interior and an open longitudinal bottom end for insertion of the medical instrument into the enclosed interior, one of the sheets being longer longitudinally than the other of the two sheets such that the open bottom end has a flap extending from the one longer sheet to a long bottom edge that extends beyond a short bottom edge of the other sheet, the pair of sheets being sealed together between the opposing lateral sides and the top and bottom ends along one or more seam lines that are arranged in a pattern that engage and hold the detection mechanism to define a maximum distance of longitudinal insertion against travel toward the top end when the detection mechanism is inserted through the enclosed interior and moved toward the top end within the interior as far toward the top end as the detection mechanism can be moved.

The one or more seam lines are typically disposed between the sides of the bag in an arrangement that slidably engages the detection mechanism when the detection mechanism is inserted through the enclosed interior and moved toward the top end.

The detection mechanism typically has a longest dimension of certain distance, the seam lines being disposed between the sides of the bag a maximum distance apart from each other or from the sides of the bag, that is less than the distance of the longest dimension of the detection mechanism such that the detection mechanism engages against and is held by the seam lines.

The sealed top end is preferably attached along a line of perforations to a manifold, the perforations enabling manual tearing away of the bag from the manifold. The seam lines can comprise a pair of separate lines formed as mirror images of each other around a longitudinal center of the enclosure. The seam lines are preferably arranged such that the detection mechanism is routed between the seam lines on longitudinal movement of the detection mechanism from the bottom end toward the top end of the enclosure.

The seam lines can form a generally triangular or conical space between the seam lines within the interior of the enclosure. Such a triangular or conical space can be truncated at its top end.

The detection mechanism has a longest dimension of certain distance and the seam lines can be separated apart from each other around the center of the enclosure a minimum distance that is less than the certain distance of the longest dimension of the detection mechanism.

In another aspect of the invention there is provided, a disposable bag for maintaining sterility of a medical instrument, the instrument comprising a detection mechanism for engagement with an examination surface of a subject to be examined for a signal generated by the subject through the examination surface, the detection mechanism having a longest dimension of certain distance, the bag comprising:

A pair of flexible sheets comprised of a polymeric material, the sheets having a thickness through which the detection mechanism can sense the signal generated by the subject when the detection mechanism is held in engagement against the examination surface with a sheets disposed between the detection mechanism and the examination surface, the pair of sheets being arranged in parallel to each other and sealed along opposing lateral sides extending longitudinally from a top end to a bottom end, the top end being sealed and the bottom end being open such that the sheets form an enclosed an enclosed interior with an open longitudinal bottom end for insertion of the medical instrument through the bottom end into the enclosed interior, one of the sheets being longer longitudinally than the other of the two sheets such that the open bottom end has a flap extending from the one longer sheet to a long bottom edge that extends beyond a short bottom edge of the other sheet, the pair of sheets being sealed together between the opposing lateral sides and the top and bottom ends along one or more seam lines that are arranged in a pattern that engage and hold the detection mechanism to define a maximum distance of longitudinal travel of the detection mechanism toward the top end when the detection mechanism is inserted through the enclosed interior and moved toward the top end within the interior as far toward the top end as the detection mechanism can be moved longitudinally.

In another aspect of the invention there is provided a method of examining a subject having a selected examination surface, the examination being conducted with a detection mechanism that senses a signal generated by the subject through the examination surface on engagement of the detection mechanism against the examination surface, the detection mechanism having a longest dimension of certain distance, the method comprising:

selecting a flexible polymeric sheet material that is transmissive to the signal generated by the subject through the examination surface forming an enclosure comprised of a pair of generally parallel arranged sheets of the selected polymeric sheet material by sealing the sheets along opposing lateral sides of the sheets that extend longitudinally from a top end to a bottom end of the enclosure, sealing the top end of the sheets to form a sealed top end of the enclosure and an interior enclosed between the sealed lateral sides and the sealed top end, forming a longitudinal length of one of the sheets to be longer than a longitudinal length of the other of the sheets such that an open bottom end is formed having a flap that extends from the one longer sheet to a bottom edge that extends longitudinally beyond a bottom edge of the other sheet, forming one or more seam lines between the sheets arranged between the lateral sides in a pattern that enables the seam lines to engage and hold the detection mechanism to define a maximum distance of longitudinal insertion against travel toward the top end when the detection mechanism is inserted through the enclosed interior and moved toward the top end within the interior as far toward the top end as the detection mechanism can be moved;

inserting the detection mechanism through the open bottom end and moving the detection mechanism longitudinally toward the top end;

manually engaging the detection mechanism inserted within the interior against the examination surface of the subject with a polymeric sheet being disposed between the examination surface and the detection mechanism.

In such a method the detection mechanism is typically inserted through the open bottom end and fully inserted longitudinally within the interior as far toward the top end as the detection mechanism can be moved.

In such a method, multiple enclosures can be formed as a collection of enclosures attached to a holding mechanism, each enclosure being attached at its top end to a manifold by a series of perforations, the perforations enabling manual tearing away of an enclosure from an associated manifold, the method preferably further comprising:

manually tearing away a first enclosure from an associated manifold along the perforations and performing an examination with a detection mechanism inserted with the interior of the first torn away enclosure;

disposing the first torn away enclosure subsequent to the examination; and, manually tearing away a second enclosure from an associated manifold along the perforations and performing an examination with the detection mechanism inserted with the interior of the second torn away enclosure.

In such a method, the detection mechanism can have a longest dimension having a certain distance and the seam lines can be disposed between the sides of the bag a maximum distance apart from each other or from the sides of the bag, that is less than the certain distance of the longest dimension of the detection mechanism such that the detection mechanism engages against and is held by the seam lines.

In such a method, the seam lines can be formed as a pair of separate lines formed as mirror images of each other around a longitudinal center of the enclosure.

BRIEF DESCRIPTION OF FIGURES

FIG. 5 is a front plan view of an embodiment of the invention showing a hook attached to the top flap of the bag.

FIG. 6 is a side view of FIG. 5.

FIG. 7 is a perspective view of the hook containing collar component shown in FIG. 5.

FIG. 8 is an enlarged perspective view of the flap portion of the FIG. 5 device.

FIG. 13 is a perspective view of another embodiment of a bag according to the invention having an adhesive disposed on an upper corner portion of the inner wall surface of the bag.

FIG. 14 is a view similar to FIG. 13 showing a stethoscope inserted into the FIG. 13 bag with the cable portion of the stethoscope adhered to the adhesive.

FIG. 15 is a perspective view of another embodiment of a bag according to the invention having a pair of flaps disposed on an inner wall surface of the bag.

FIG. 16 is a view similar to FIG. 15 showing a stethoscope inserted into the FIG. 15 bag with the head of the stethoscope engaged by a flap.

DETAILED DESCRIPTION OF INVENTION

Figure 1:
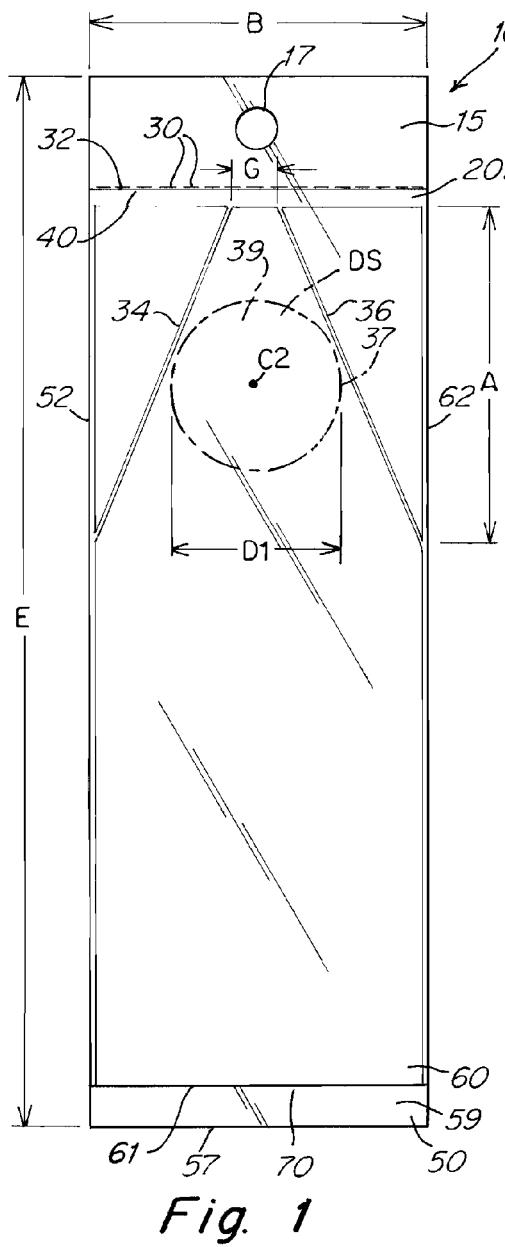
FIG. 1 is a top plan view of an individual bag according to the invention.
Figure 2:
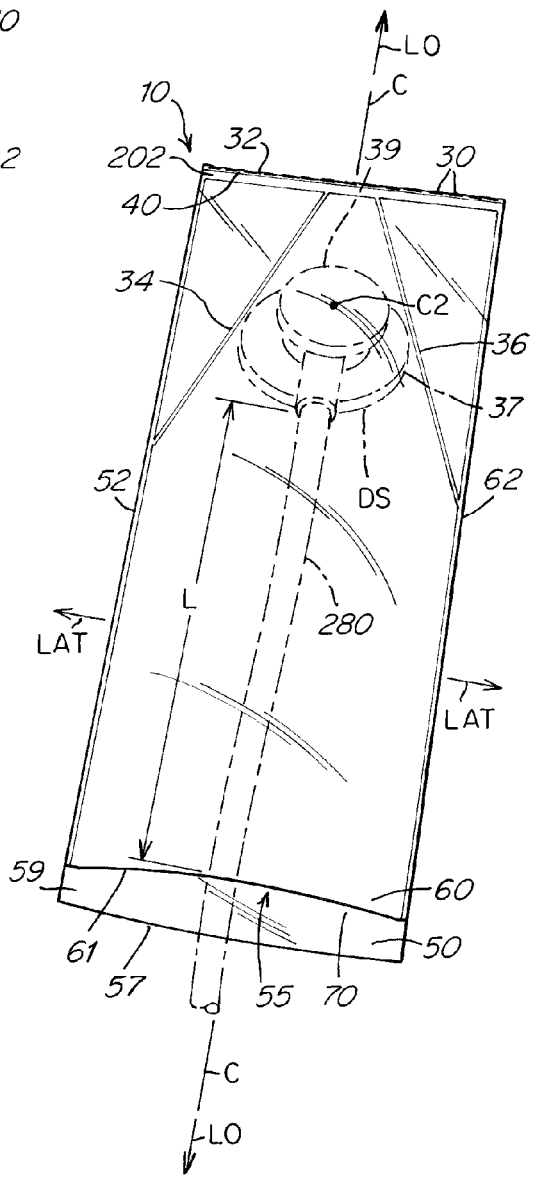
FIG. 2 is a top perspective view of an individual bag according to the invention showing a stethoscope received fully within the bag in an operational position for use on a patient.

FIGS. 1, 2 show an individual bag according to the invention comprised of a first upper sheet 60 that is connected along side edges 52, 62 and along a top seal strip 202 to an opposing parallel arranged bottom sheet 50. Each bag is interconnected to a mounting or manifold strip 15 of plastic along a relatively thin line 32 of polymeric material that has a series of perforations 30 extending from one side edge 52 of the connected sheets across the lateral width B of the bags 300 to the other opposing side edge 62. The line 32 has a sufficient number of perforations 30 such that an individual bag 10 can be readily detached along the line 32 of perforations 30 from the manifold or mounting strip 15 by steadily pulling a bag downwardly DF away from the strip 15 by hand under relatively light manual force.

As shown in FIG. 1, each bag has a width B, a height E and seams 34, 36 formed between the top and bottom sheets 50, 60 in an arrangement as shown for example to form a truncated triangle or V or cone at the top end of the interior volume 55, FIG. 1a, of the bags 10. The seams 34, 36 that form the triangle or cone at the top enclosed end 40 of the bag 10 (or other stethoscope head receiving configuration such as a curve), serve to slidably engage the circumferential edge 37 of the head 39 of the medical instrument (such as a stethoscope) when the stethoscope head is manually inserted into the interior 55 and pushed longitudinally LO upward within the interior 55 toward the closed end 40. On further pushing, urging of the head 39 toward the closed end 40, the circular 37 head is slid along one or the other or both of the seams into a position where the center C2 of the circle 37 is slid into approximate alignment with the lateral center C of the bag 10. The head 39 is thus stabilized in position within the interior 55 of the bag 10 on and around the circumference of the head 39. The head 39 is a device that is capable of detecting select signals, sounds, vibrations and the like generated by a patient's body such as in a stethoscope instrument 283 that has a cable or signal communication tube 280 interconnected between the sensing head or detector and the hear jacks 280e of the instrument 280.

The width B and height E and arrangement of the seams 34, 36 are selected relative to the diameter D1 of the head 37 so that the circumference 37 of the head 39 fits easily within the open end 70 of the distal-most end of a bag 10, and also fits readily within the interior enclosed space 55 within the bags. The seams 34, 36 are also arranged in a configuration, such as the equilateral triangular configuration shown in FIG. 1, such that the diameter D1 head 39 of the inserted device is readily receivable between and by and engageable with the seams 34, 36 and is also readily receivable within the space at the top end of the bags that is formed by and between the seams 34, 36. As shown in FIG. 1, in a typical embodiment, the width B is between about 3 and 5 inches (e.g. 4 inches), the height E is between about 10 and 14 inches (e.g. 12 inches), the distance A (height of the truncated triangle formed by seams 34, 36 is between about 3 and about 5 inches (e.g. about 4 inches). The seams 34, 36 are formed at the closed end of the bags 10. The height E is selected such that when the circumference 37 of the head 39 is fully disposed within the space defined, bordered or enclosed by the seams 34, 36, a substantial length L of the communicating tube 280 component of the stethoscope is also enclosed within the interior 55 of the bag, typically from about 8 to about 15 inches in length of communication tubing.

Figure 4:
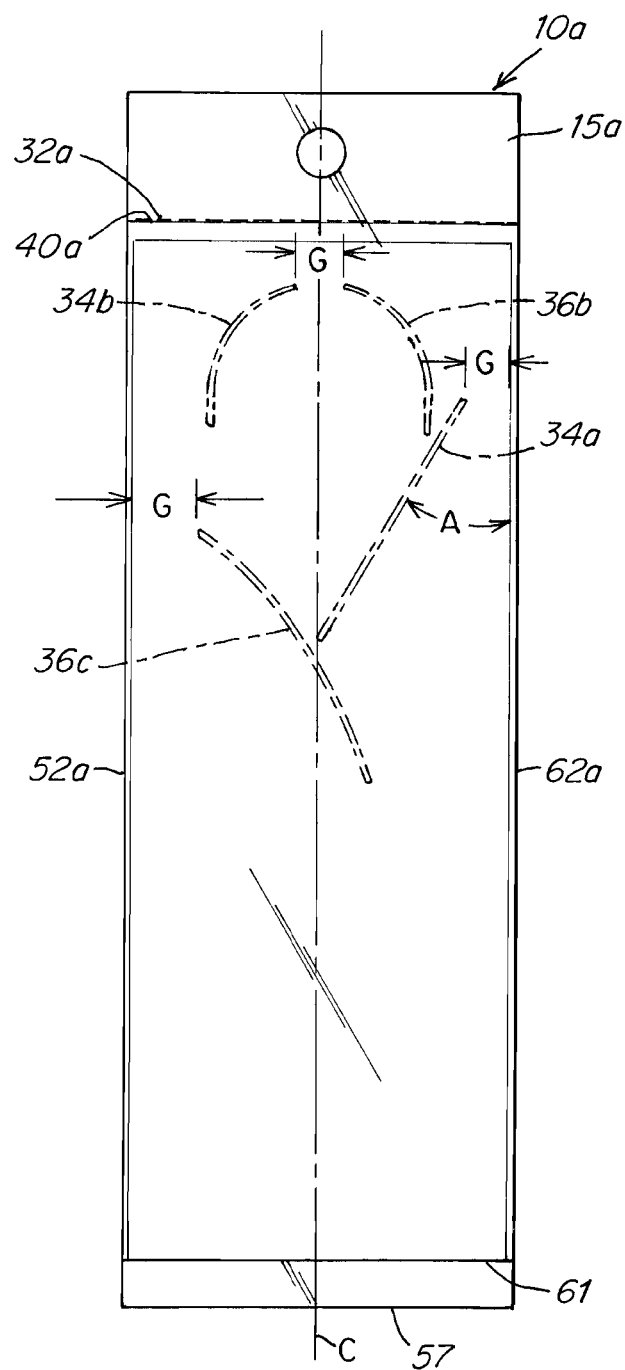
FIG. 4 is a top schematic view showing a variety of alternative seam lines that could be used in forming a bag according to the invention.

As shown in schematic in FIG. 4, the seam line or lines of a bag 10a can comprise a single seam line 34a disposed at an angle A relative to the longitude of the bag 10a, the seam line 34a acting to capture and hold the head 39 of the instrument between the line 34a and the side 62a. Alternatively the seam lines can comprise a pair of opposing seam lines 34b, 36b that are curved in part or curvilinear, the lines 34a, 36a shown as being mirror images of each other around center line C. Also alternatively, the seam lines can comprise a line 36c that is curved or curvilinear which can capture the head 39 between the line 36c and the side or edge 52a. In each embodiment, the head 39 of the instrument has a longest dimension having a length D1 that is larger than the distance G between the longitudinally top-most point of the seam line or lines and the next closest seam or seal or the seal side 52a or 62a of the bag 10a. In each embodiment, the seam line or lines have at least a portion of their contour that is disposed at an angle of between 1 and 89 degrees relative to the longitude of the bag such that when the head 39 is moved manually in the longitudinal direction from the bottom 57 toward the top end 40a the circumference 37 of the instrument will slidably engage the angled portion of the seam lines and be guided between the seam lines 34b, 36b or between a seam line 34a or 34c and a side 62a, 52a.

As can be readily imagined, one of the sealed sides or edges, 52, 62 of a bag 10 is typically formed in the fabrication process by application of between between an upper 50 and lower 60 sheet, the other sealed side or edge being formed by simply folding a single sheet of flexible polymeric material over onto itself.

As shown in FIG. 2, the perforated seam or separation line 32 is spaced slightly upstream beyond the top sealed edge 40 of the bag 10 by a top end seam 32f such that when bag 10 is separated from bag 10a, FIG. 2, the top edge 40 of bag 10 is fully sealed or closed along its top edge 40 by a seam 202.

Because the two opposing sheets 50, 60 are typically adhered to each other by electrostatic, moisture or other forces, sheet 50 is formed to have a longer length than sheet 60, the two sheets 50, 60 being attached to each other in an arrangement where the end 57 of sheet 50 extends longitudinally beyond the end 61 of sheet 60 leaving a short-in-length end flap 59 to sheet 50 extending beyond the terminal edge 61 of sheet 60. The flap 59 enables ready separation of the two sheets 50, 60 along the width B of the flap 59 by hand thus enabling the user to readily grab/engage the flap 59 with two fingers and separate the bottom sheet 50 from the top sheet 60 to create an aperture between the terminal edge 61 and the terminal flap 57 readily enabling the medical instrument to be quickly and easily inserted into the interior space 55 of the otherwise sealed bag.

Figure 3:
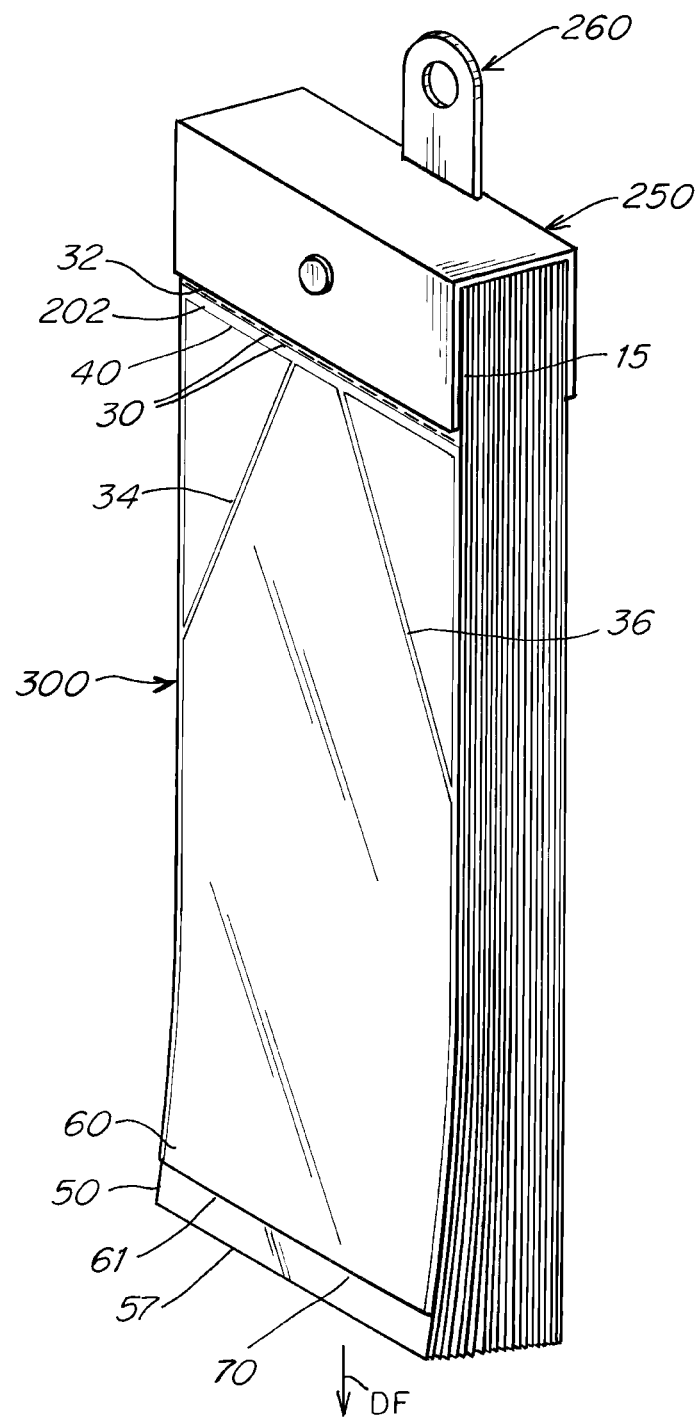
FIG. 3 is a side isometric view of a stack of successively mounted bags according to the invention mounted or attached to a holder that are readily detachable from a manifold or holder strip that is attached/connected to the holder.

FIG. 3 illustrates a collection of individual bags 300, each separately comprising a connector strip 15, closed end strip 202 and pair of opposing sheets 50, 60, the multiplicity of bags being arranged in a stacked format, one bag next to the other in parallel stacked sequential arrangement. The stack of the plurality of bags 300 are all attached by conventional means to a holder 250 that is connected to the top connector strips 15 of the bags 300. The connector or support 250 is provided with a hanger mechanism 260 such that the can be mounted on a hook, nail or other supporting structure. Also as shown in FIGS. 1, 2, a small aperture 17 is provided at about the center of the width of the manifold 15 and seam 202 for alternatively mounting the collection of bags 300 on a nail or rod.

The apparatus is preferably provided to a user in the format of a plurality of bags that are attached to a common support, rail, hanger, bar or the like (hereinafter individually and collectively referred to as a "support") and are separable from the support by pulling an individual bag attached to the support with relatively minor manual pulling force away from the support. The system typically comprises a support 250 to which is attached a series of flattened plastic bags arranged in a sequentially stacked one-next-to-each-other arrangement. The last bag on the outside of the stack is arranged such that a closed or sealed end of the bag is tearably attached to a manifold or mount 15 that is typically attached to a support 250 that holds the entire stack together as and in an arrangement as a stack. The sealed end 202 of an individual bag 10 is readily detachably attached to the mount or manifold portion of plastic material 15 via a series of perforations 30 extending from one side 52 of a bag to another side 62 of the bag at the terminal edge 32 of the closed 202 end of a bag 10. When the last outside-most bag in the series of bags in the stack is torn away from and detached from a manifold strip 15 of plastic, the next bag in the stack is immediately visually and manually accessible to be detached from the next manifold portion of plastic in the stack in the same manner that the previous outside-most bag had been detached.

Each bag 10 is held in a stationary position by virtue of the mount/manifold portion 15 of the apparatus being attached or secured to the support or holder 250 which itself is typically mounted via a handle 260 or other equivalent mechanism to a stationary hook, nail, rod or the like which is attached to a stationary structure such as a structural wall or item of furniture or hospital equipment that is stationarily positioned within a room where the bags 10 of the invention would be normally used by a health provider using the medical equipment to be inserted in a bag 10. With the entire stack of bags being stationarily secured to a wall or other mount, the user can manually engage and exert a downward pulling force DF by hand on the sheets 50, 60 of an individual bag 10 and effect a tearing away of a bag 10 along the perforations line/curve 32 to separate the sealed seam 202 and thus an entire bag from the mount/manifold 15.

Most preferably the series of bags in the stack 300 that are attached to the support 250 are all constructed and arranged such that an aperture is disposed in about the lateral center or middle of the mount/manifold 15.

Each bag in the stack typically comprises two generally square or rectangular sheets 50, 60 of thin flexible polymeric material that are arranged in parallel one on top of the other and sealably attached to each other along their side edges 52, 62 and further attached to each other along their top sealed edges via a widened seam 202. The bottom edges 57, 61 of the two sheets 50, 60 that comprise an individual bag 10 are typically not sealed to each other thus forming an opening 70 along the bottom edge 61 of the square or rectangular assembly of the two parallel sheets that are attached to each other along their top and side edges.

One of the two parallel one-on-top-of-the-other sheets 50 is preferably longer in length than the other of the two sheets 60 so that when the top and side edges are sealed, the bottom end or edge 57 of one sheet 50 extends beyond the bottom end or edge 61 of the other sheet 60 thus enabling a user of the bag to readily visually and manually locate and separate the two sheets from each other at the bottom edge of the two sheets thus enabling the bag to be readily opened 70 such that the medical device 39 to be inserted through the opening 70 is facilitated.

Each individual bag 10 typically has a generally triangular or conical configuration formed into the structure of the bag by a pair of mirror image seam lines 34, 36 arranged to form a truncated at-the-top triangle or cone within the interior 55 of the bag at the top closed end of the bag extending along longitudinal length A of the bag 10 such that when a circular head 37 of a stethoscope 39 is forcibly inserted completely within the interior 55 of a bag toward the top edge 40 of the bag 10, the circumference 37 of the stethoscope head having a diameter D1 is lodged between the two seam lines 34, 36 that form the truncated triangular or conical interior top or closed end of the bag. As shown in FIG. 1, the apex of the triangle or V formed by the seams 34, 36 is typically not complete leaving a gap G between the top or terminal apex end of the angled seam lines 34, 36.

As shown, the distance G at the top longitudinal end of the truncated V shaped seam lines 34, 36 is the minimum spaced apart distance between the seam lines around the center C of the bag. The distance G is less than the distance or length D1 of the diameter of the instrument head 39 which is the longest dimension of the instrument along any straight line such that the instrument head 39 cannot pass between the seam lines 34, 36.

Once the stethoscope head is inserted within the interior 55 of a bag, the head 39 is moved from the open end 70 toward the closed end 40. In the course of inserting and moving the head 39 longitudinally LO toward the closed end, the circumferential edges 37 engage on or the other or both of the seams 34, 36. On further movement longitudinally LO toward the top end 40, the head 39 eventually is positioned in the position shown in FIG. 1 such that the circumference 37 of the head 39 engages the seam lines 34, 36 and guides and moves the center C2 of the head toward the lateral center C of the bag. The angled orientation of the V shaped seam lines relative to the longitude LO of the bag serves to slidably engage the circumferential edges 37 of the catheter head 39 and slidably guide the center of the circular or cylindrical head 39 into a stable position along the latitude LAT of the bag that is in alignment/intersection with the lateral LAT center C of the bag 10. The seam lines 34, 36 are seals or permanently fused portions of and between the two sheets 60. Such seams 34, 36 are formed in a conventional manner via application of heat to the outer surfaces of the sheets 60 while engaged against each other, the heat being applied in local concentration along the length of the desired contour of the line or lines 34, 36. Seam formation is typically carried out using a heat press or other conventional process and apparatus for forming such seam lines.

Once the head 39 has been fully inserted longitudinally toward the closed top end 40 of the bag 10 and positioned such that the center C2 is in approximate alignment with the center C, the health provider or user manually positions the head 39 such that a detection surface DS is placed with pressure by manual force against a complementary surface of a patient or subject to be examined, one of the sheets 50, 60 being disposed between the surface of the subject being examined and the detection surface DS of the head 39. The sensitivity of the detection surface DS is high enough and sensitive enough and the thickness of the sheets 50, 60 are selected to be of such a degree or thickness to enable the instrument head and detection surface DS to readily receive and detect the desired information such as electrical signals, sound waves, heat or the like from the surface of the subject that the detection surface DS is capable of detecting and transmitting to through the communication tube 280 of the instrument.

Once the user has performed the measurement using the head 39 contained within the bag 10, the bag 10 that was just used to contain and cover the operative surface DS of the instrument 39 is then removed, discarded and another new bag 10 from the stack 300 is torn off from the support 250 for use with another new patient for another cycle of measurement by the user. Each successive individual patient is thus ensured of not being contacted with the operative surface DS of the device but rather by the outside surface of one or the other of the sheets 50, 60 of a new individual bag 10 during each successively performed procedure.

In one embodiment the polymeric material comprising the bags comprises a sheet of flexible material having a thickness of typically less than about 500 microns and more typically less than about 100 microns. The sheet material itself typically comprises a woven or punch formed fabric, a paper material or a solid polymeric material comprised of one or more polymers such as polyethylene, polypropylene, polyester or the like.

The perforations provided along the attachment seams between a manifold and the closed end of a bag are preferably configured to be of such a size and spaced apart from each other from side to side such that an individual bag can be readily detached from a manifold strip of plastic material by use of a normal pulling force using the hand and arm of a human being.

The geometrical area or shape of a sheet 50, 60 according to the invention can have any one of an unlimited number of forms such as square, rectangular, triangular, oval or egg-shaped.

FIGS. 5-8 show an embodiment of the invention where a hook device 47 comprises a tubular mount 47m having a hollow bore 47c that is complementary in diameter to the diameter of the cable or signal communication tube 280 of the stethoscope 283 such that the mount 47 fits snugly around the exterior surface 280es of the cable 280. A hook 47h is attached to the outer surface of the mount 47m, the hook having a pointed end or puncture member 47p for puncturing through the wall of the flap 59 of the bag 10 and thus attaching the cable 280 of the instrument to the bag 10. As shown when the hook end 47p is manually forced through the flap 59 the bag 10 is longitudinally held in a relatively stationary position relative to the detection or sensing member 39 and the cable 280 such that the flexible bag 10 does not freely move or collapse to the point where the sensing head 39 might fall outside of the interior chamber 55 of the bag.

Figure 9:
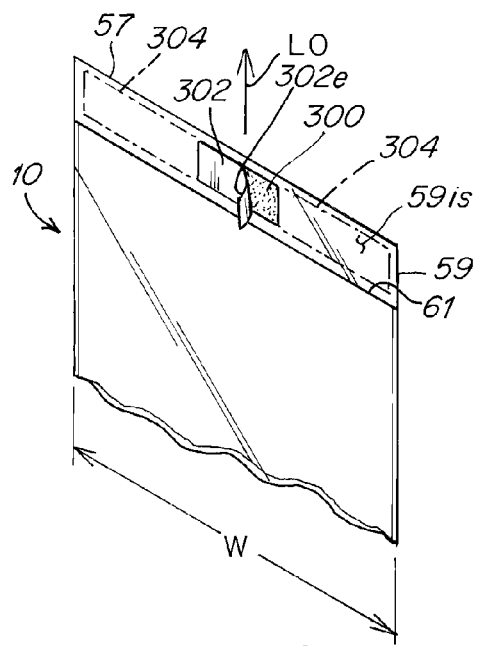
FIG. 9 is an enlarged perspective view of the flap portion of another embodiment of a bag according to the invention where a flap contains an adhesive.
Figure 10:
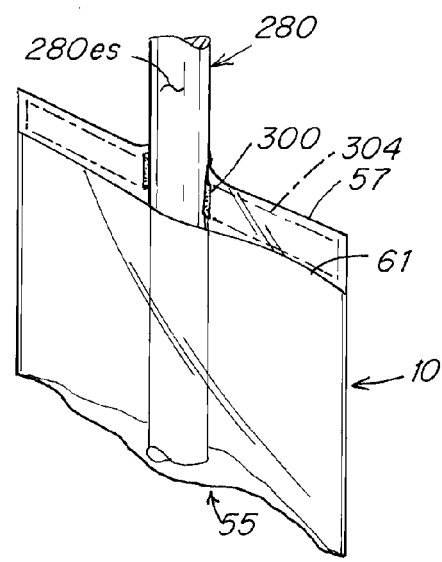
FIG. 10 is a view similar to FIG. 9 showing a stethoscope inserted into the FIG. 9 bag with the cable portion of the stethoscope adhered to the adhesive on the flap.

FIGS. 9, 10 show an embodiment of the invention where the inside surface 59is of the flap 59 has a layer of adhesive 300 attached to the surface 59is in a predetermined two-dimensional pattern such as a rectangle as shown in FIG. 9 that is large enough to readily engage and attach to a portion of the exterior surface 280es of the cable 280. As shown the adhesive can be applied to the surface 59is in any desired pattern including a pattern shown in dashed lines 304 that extends substantially the entire lateral width W of the bag 10 that is transverse to the longitude LO.

Preferably a thin sheet or film or strip 302 of flexible non-adhesive material is applied over the exposed surface of the adhesive layer 300, 304 to protect the adhesive from attaching to or attracting extraneous materials. The film or strip 302 is provided with a readily manually accessible end or tab 302e that a user can readily manually engage and pull on to remove the cover 302 when it is ready to be adhered to the surface 280es of the cable or tube component 280 of the instrument 283. As shown when the adhesive is attached to the surface 280es of the cable 280, the bag 10 is longitudinally held in a relatively stationary position relative to the detection or sensing member 39 and the cable 280 such that the flexible bag 10 does not freely move or collapse to the point where the sensing head 39 might fall outside of the interior chamber 55 of the bag.

Figure 11:
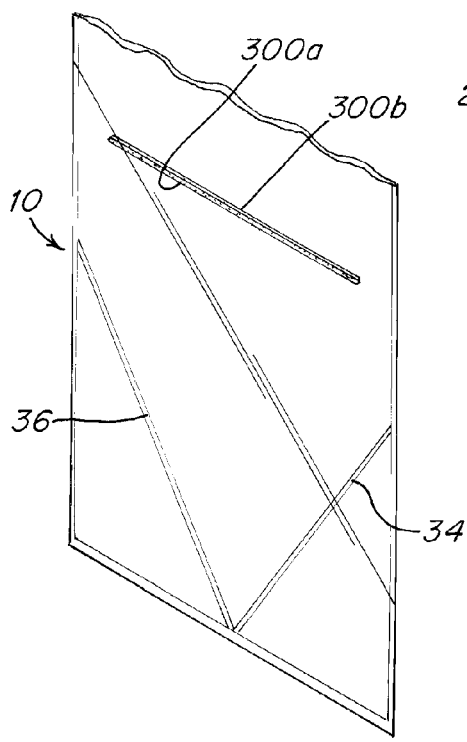
FIG. 11 is a perspective view of another embodiment of a bag according to the invention having an adhesive disposed on an inner wall surface of the bag.
Figure 12:
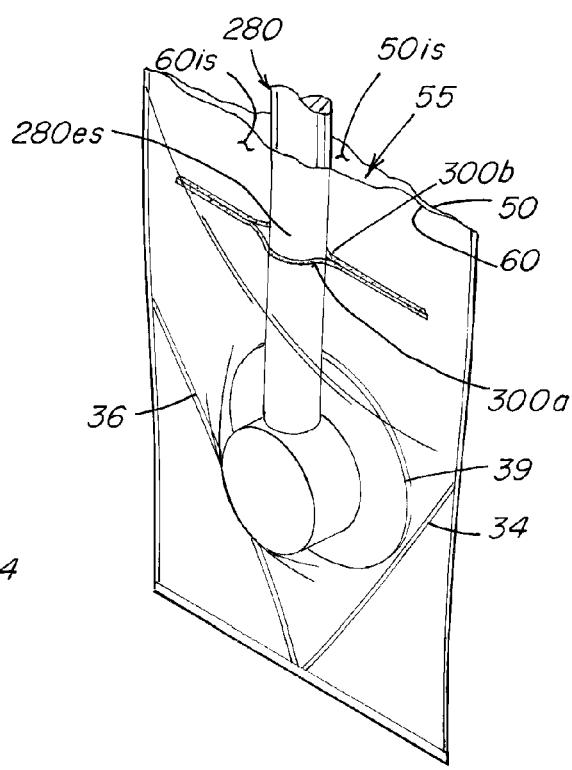
FIG. 12 is a view similar to FIG. 11 showing a stethoscope inserted into the FIG. 11 bag with the cable portion of the stethoscope adhered to the adhesive.
Figure 17:
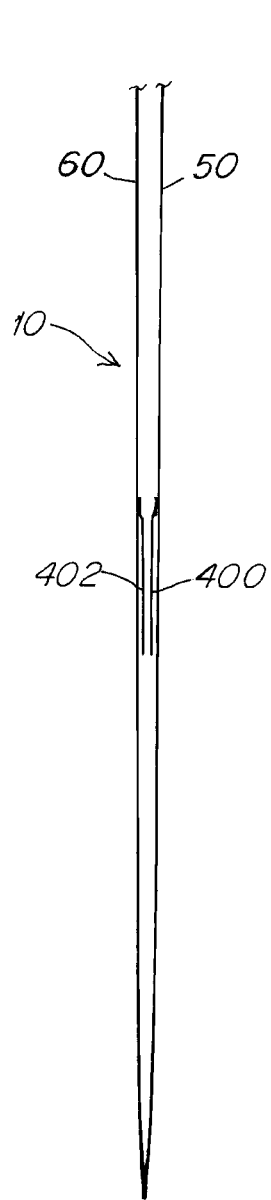
FIG. 17 is a side view of the FIG. 15 bag.
Figure 18:
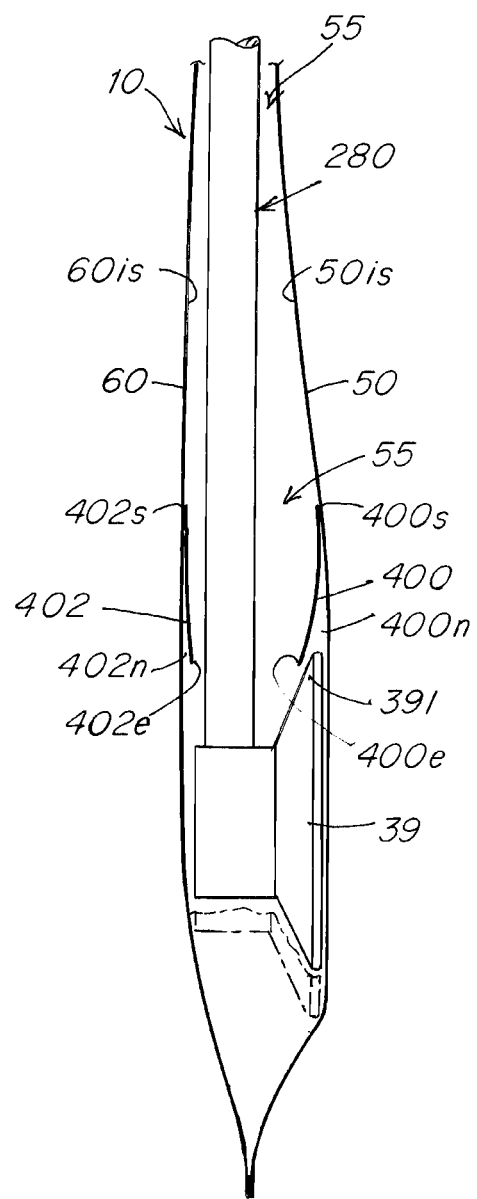
FIG. 18 is a side view of the FIG. 16 bag with the stethoscope inserted into the bag and engaged with the flap.

FIGS. 11, 12 show an embodiment where a layer of adhesive 300a, 300b is applied to either or both of two opposing inside surfaces 50is, 60is of the two opposing sheets 50, 60 that form the bag 10. The adhesive 300a, 300b is applied and disposed in a position and geometrical pattern such as a line or a rectangle as shown in FIGS. 9, 10 that is positioned such that the inside surfaces 50is, 60is can be readily manually separated along the areas where the adhesive 300a, 300b is applied and the head 39 inserted into the chamber or enclosure 55 longitudinally past the position of the adhesive 300a, 300b into engagement with the seams 34, 36 as shown in FIG. 12. Once the head 39 is inserted, the exterior surface 280es of the cable 280 can be manually engaged with one or the other or both of the adhesive layer 300a, 300b thus attaching the cable 280 to the inside surfaces 50is, 60is of one or both of the walls or sheets 50, 60 of the bag 10. Once the cable 280 is so attached to the adhesive 300a or 300b, the, the bag 10 is longitudinally held in a relatively stationary position relative to the detection or sensing member 39 and the cable 280 such that the flexible bag 10 does not freely move or collapse to the point where the sensing head 39 might fall outside of the interior chamber 55 of the bag.

FIGS. 13, 14 show an embodiment where a layer of adhesive 300c is applied in another geometrical patter in another position on one or the other or both of the inside surfaces 50is, 60is of the two opposing sheets 50, 60 that form the bag 10. As shown the adhesive layer 300c is disposed in a small rectangle at an upper corner of the open bottom end of the bag 10 such that the inside surfaces 50is, 60is can be readily manually separated along the areas where the adhesive 300c is applied and the head 39 inserted into the chamber or enclosure 55 longitudinally past the position of the adhesive 300c into engagement with the seams 34, 36 as shown in FIG. 12. Once the head 39 is inserted, the exterior surface 280es of the cable 280 can be manually engaged with the adhesive layer 300c thus attaching the cable 280 to one or the other of the inside surfaces 50is, 60is of one or both of the walls or sheets 50, 60 of the bag 10. Once the cable 280 is so attached to the adhesive 300c, the bag 10 is longitudinally held in a relatively stationary position relative to the detection or sensing member 39 and the cable 280 such that the flexible bag 10 does not freely move or collapse to the point where the sensing head 39 might fall outside of the interior chamber 55 of the bag.

FIGS. 15-18 show another embodiment where a pair of sheets or flaps 400, 402 are attached via heat seals 400s, 402 at their upper edges to the interior surfaces 50is, 60is of the two opposing sheets 50, 60 of the bag 10. The flaps 400, 402 extend across the width W of the bag 10 and are unattached at their usstream edges 400e, 402e forming a one way notch 400n, 402n that receives the lip 39l of the head 39 thus preventing the head 39 from exiting the chamber 55. In this embodiment there is provided a disposable bag 10 for maintaining sterility of a medical instrument, the instrument comprising an elongated cable 280 and a detection mechanism 39 for engagement with an examination surface of a subject to be examined for a signal generated by the subject through the examination surface, the elongated cable being interconnected to the detection mechanism at a proximal end of the cable for transmitting a signal generated by the detection mechanism to a distal end of the cable wherein the bag comprises:

a pair of flexible sheets comprised of a polymeric material, the sheets having a thickness through which the detection mechanism can sense the signal generated by the subject when the detection mechanism is held in engagement against the examination surface with one of the sheets disposed between the detection mechanism and the examination surface, the pair of sheets 50, 60 being arranged in parallel to each other and sealed along opposing lateral sides 52, 62 that extend longitudinally LO from a top end to a bottom end, the top end being sealed and the bottom end being open such that the sheets form an enclosed interior chamber with an open longitudinal bottom end for insertion of the detection mechanism into and longitudinally through the enclosed interior chamber a selected insertion distance from the open bottom end toward the sealed top end, one or the other of the pair of sheets having a flap sheet sealed at an upper edge of the flap sheet across the width of one or the other or both of the interior surfaces of the pair of sheets, the sealed flap sheets forming a notch that receives a circumferential edge of the detection mechanism to prevent the detection mechanism from travelling longitudinally downstream through the open bottom end of the bag.

It is to be understood that the foregoing description is intended to illustrate and not limit the scope of the invention.

What is claimed is:

1. A disposable bag including and maintaining sterility of a medical instrument, the instrument comprising an elongated cable having a cable length and a detection mechanism for engagement with an examination surface of a subject to be examined for a signal generated by the subject through the examination surface, the elongated cable being interconnected to the detection mechanism at a proximal end of the cable for transmitting a signal generated by the detection mechanism to a distal end of the cable, wherein the bag comprises:

a pair of flexible opposing sheets comprised of a polymeric material, the sheets having a thickness through which the detection mechanism can sense the signal generated by the subject when the detection mechanism is held in engagement against the examination surface with one of the sheets disposed between the detection mechanism and the examination surface, the pair of sheets having interior surfaces and being arranged in parallel to each other and sealed along opposing lateral sides that extend longitudinally from a top end to a bottom end, the top end being sealed and the bottom end being open such that the sheets form an enclosed interior chamber with an open longitudinal bottom end for insertion of the detection mechanism into and longitudinally through the enclosed interior chamber a selected insertion distance from the open bottom end toward the sealed top end, one of the pair of sheets being longer longitudinally than the other of the pair sheets forming a flap that extends from the one longer sheet to a longer bottom edge that extends longitudinally beyond a shorter bottom edge of the other of the pair of sheets, the bag having a selected longitudinal length relative to the cable length such that upon insertion of the detection mechanism through the enclosed interior chamber along the selected insertion distance, the cable extends longitudinally from the detection mechanism through the enclosed interior chamber and further through the open bottom end to at least the longer bottom edge of the one longer sheet, one or the other or both of the interior surfaces of the two opposing sheets having an attachment mechanism attachable to at least a portion of the cable that extends from the detection mechanism to at least the longer bottom edge such that the detection mechanism is held within the enclosed interior chamber.

2. The bag of claim 1 wherein the attachment mechanism comprises a layer of adhesive material disposed on an interior surface of the flap in a selected two dimensional pattern and the cable has an outside surface that is adhesively attachable to the adhesive material, the layer of adhesive material being disposed on the interior surface of the flap in an arrangement such that at least a portion of the outside surface of the cable that extends to at least the longer bottom edge of the one longer sheet of the bag is manually compressible against at least a portion of the adhesive layer and adhesively attachable thereto.

3. Method of examining a patient with a medical instrument having a cable and detection mechanism according to claim 1 wherein the detection mechanism detects a selected signal generated by patient, the method comprising inserting the detection mechanism in a bag according to claim 1, attaching the cord to the attachment mechanism and examining the patient with the detection mechanism inserted in the bag.

4. A disposable bag including and maintaining sterility of a medical instrument, the instrument comprising an elongated cable having a cable length and a detection mechanism for engagement with an examination surface of a subject to be examined for a signal generated by the subject through the examination surface, the elongated cable being interconnected to the detection mechanism at a proximal end of the cable for transmitting a signal generated by the detection mechanism to a distal end of the cable, wherein the bag comprises:

a pair of flexible sheets comprised of a polymeric material, the sheets having a thickness through which the detection mechanism can sense the signal generated by the subject when the detection mechanism is held in engagement against the examination surface with one of the sheets disposed between the detection mechanism and the examination surface, the pair of sheets being arranged in parallel to each other and sealed along opposing lateral sides that extend longitudinally from a top end to a bottom end, the top end being sealed and the bottom end being open such that the sheets form an enclosed interior chamber with an open longitudinal bottom end for insertion of the detection mechanism into and longitudinally through the enclosed interior chamber a selected insertion distance from the open bottom end toward the sealed top end, the pair of sheets each having an interior surface facing each other, one or the other of the interior surfaces having a layer of adhesive material disposed thereon in a selected two dimensional pattern at a longitudinal position between the top and bottom ends such that the adhesive material on an interior surface of one sheet opposes and can make contact with the interior surface of an opposing sheet, the bag having a selected longitudinal length relative to the cable length such that upon insertion of the detection mechanism through the enclosed interior chamber along the selected insertion distance, the cable extends longitudinally from the detection mechanism through the enclosed interior chamber and further through the open bottom end to at least the longer bottom edge of the one longer sheet, the cable having an outside surface that is adhesively attachable to the adhesive material, the layer of adhesive material being disposed on the interior surface of the flap at a selected longitudinal position less than the selected insertion distance in an arrangement such that at least a portion of the outside surface of the cable that extends from the detection mechanism longitudinally to at least the selected longitudinal position of the adhesive material is manually compressible against and adhesively attachable to the adhesive material.

5. The bag of claim 4 wherein the adhesive material is disposed on both of the interior surfaces of the opposing sheets of the bag in the selected two dimensional pattern.

6. Method of examining a patient with a medical instrument having a cable and detection mechanism according to claim 4 wherein the detection mechanism detects a selected signal generated by patient, the method comprising inserting the detection mechanism in a bag according to claim 4, attaching the cord to the layer of adhesive material and examining the patient with the detection mechanism inserted in the bag.

7. A disposable bag including and maintaining sterility of a medical instrument, the instrument comprising an elongated cable having a cable length and a detection mechanism for engagement with an examination surface of a subject to be examined for a signal generated by the subject through the examination surface, the elongated cable being interconnected to the detection mechanism at a proximal end of the cable for transmitting a signal generated by the detection mechanism to a distal end of the cable, wherein the bag comprises:

a pair of flexible opposing sheets comprised of a polymeric material, the sheets having a thickness through which the detection mechanism can sense the signal generated by the subject when the detection mechanism is held in engagement against the examination surface with one of the sheets disposed between the detection mechanism and the examination surface, the pair of sheets having interior surfaces and being arranged in parallel to each other and sealed along opposing lateral sides that extend longitudinally from a top end to a bottom end, the top end being sealed and the bottom end being open such that the sheets form an enclosed interior chamber with an open longitudinal bottom end for insertion of the detection mechanism into and longitudinally through the enclosed interior chamber a selected insertion distance from the open bottom end toward the sealed top end, one of the pair of sheets being longer longitudinally than the other of the pair sheets forming a flap that extends from the one longer sheet to a longer bottom edge that extends longitudinally beyond a shorter bottom edge of the other of the pair of sheets, the bag having a selected longitudinal length relative to the cable length such that upon insertion of the detection mechanism through the enclosed interior chamber along the selected insertion distance, the cable extends longitudinally from the detection mechanism through the enclosed interior chamber and further through the open bottom end to at least the longer bottom edge of the one longer sheet, wherein one or the other or both of the interior surfaces of the two opposing sheets has a layer of adhesive material disposed on an interior surface of the flap in a selected two dimensional pattern and the cable has an outside surface that is adhesively attachable to the adhesive material, the layer of adhesive material being disposed on said one or the other or both of the interior surfaces in an arrangement such that at least a portion of the outside surface of the cable that extends to at least the longer bottom edge of the one longer sheet of the bag is manually compressible against at least a portion of the adhesive layer and adhesively attachable thereto.

8. Method of examining a patient with a medical instrument having a cable and detection mechanism according to claim 7 wherein the detection mechanism detects a selected signal generated by patient, the method comprising inserting the detection mechanism in a bag according to claim 7, attaching the cord to the layer of adhesive material and examining the patient with the detection mechanism inserted in the bag.

* * * * *